United States Patent
Okamoto et al.

(10) Patent No.: US 9,983,278 B2
(45) Date of Patent: May 29, 2018

(54) MAGNETIC RESONANCE IMAGING APPARATUS

(71) Applicant: TOSHIBA MEDICAL SYSTEMS CORPORATION, Otawara-Shi, Tochigi (JP)

(72) Inventors: Kazuya Okamoto, Saitama (JP); Manabu Ishii, Otawara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1322 days.

(21) Appl. No.: 13/896,440

(22) Filed: May 17, 2013

(65) Prior Publication Data

US 2013/0249560 A1 Sep. 26, 2013

Related U.S. Application Data

(63) Continuation of application No. PCT/JP2012/062715, filed on May 17, 2012.

(30) Foreign Application Priority Data

May 20, 2011 (JP) ................. 2011-114229

(51) Int. Cl.
*G01R 33/34* (2006.01)
*G01R 33/36* (2006.01)
*A61B 5/055* (2006.01)

(52) U.S. Cl.
CPC .............. *G01R 33/34* (2013.01); *A61B 5/055* (2013.01); *G01R 33/3657* (2013.01); *G01R 33/3664* (2013.01); *G01R 33/34076* (2013.01)

(58) Field of Classification Search
CPC ................ G01R 33/34; G01R 33/3657; G01R 33/3664; G01R 33/34076; A61B 5/055
See application file for complete search history.

(56) References Cited

U.S. PATENT DOCUMENTS 4,684,895 A * 8/1987 Misic ................. G01R 33/3678
324/309
5,371,466 A * 12/1994 Arakawa ............ G01R 33/3685
324/318
(Continued)

FOREIGN PATENT DOCUMENTS

CN 101266287 A 9/2008
CN 101652672 A 2/2010
(Continued)

OTHER PUBLICATIONS

Office Action dated Jun. 4, 2014 in CN Patent Application No. 201280000471.1.
(Continued)

*Primary Examiner* — Dixomara Vargas
(74) *Attorney, Agent, or Firm* — Nixon & Vanderhye P.C.

(57) ABSTRACT

According to one embodiment, an MRI apparatus includes a data acquisition system and a control system. The data acquisition system acquires MR signals from a subject. The control system acquires the MR signals by controlling the data acquisition system to generate image data. The data acquisition system has a WB coil, an RF coil and a breaker circuit. The WB coil applies the RF magnetic field to the imaging area. The RF coil applies the RF magnetic field to the imaging area when an RF pulse has been applied from the control system through a connector. The RF coil is set inside the WB coil. The breaker circuit electrically breaks a part of a circuit constituting the RF coil when the connector of the RF coil has been disconnected to the control system.

5 Claims, 11 Drawing Sheets

(56) References Cited

U.S. PATENT DOCUMENTS

| | | | | |
|---|---|---|---|---|
| 5,376,885 | A * | 12/1994 | Arakawa | G01R 33/3685 324/318 |
| 5,386,191 | A * | 1/1995 | McCarten | G01R 33/341 324/318 |
| 6,501,274 | B1 * | 12/2002 | Ledden | G01R 33/3453 324/318 |
| 6,727,698 | B1 * | 4/2004 | Eydelman | G01R 33/34053 324/318 |
| 7,012,429 | B1 * | 3/2006 | Ledden | G01R 33/3453 324/318 |
| 7,747,310 | B2 * | 6/2010 | Misic | G01R 33/285 600/423 |
| 7,885,704 | B2 * | 2/2011 | Misic | A61B 5/055 600/423 |
| 8,228,065 | B2 | 7/2012 | Wirtz et al. | |
| 8,269,499 | B2 | 9/2012 | Hamamura et al. | |
| 8,390,287 | B2 * | 3/2013 | Crozier | G01R 33/34046 324/309 |
| 8,989,841 | B2 * | 3/2015 | Misic | G01R 33/285 600/410 |
| 2011/0291655 | A1 * | 12/2011 | Hamamura | G01R 33/3642 324/318 |

FOREIGN PATENT DOCUMENTS

| | | |
|---|---|---|
| JP | 62-005160 | 1/1987 |
| JP | 63-115550 | 5/1988 |
| JP | 4-020328 | 1/1992 |
| JP | H07-171135 | 7/1995 |
| JP | 2009-142646 | 7/2009 |

OTHER PUBLICATIONS

Non-English Written Opinion for PCT/JP2012/062715 dated Jun. 19, 2012.

Notification of Transmittal of Translation of the International Preliminary Report on Patentability in PCT/JP2012/062715 dated Nov. 28, 2013.

International Search Report for PCT/JP2012/062715, dated Jul. 9, 2012.

U.S. Appl. No. 12/791,166, Hamamura et al., filed Jun. 1, 2010.

* cited by examiner

MAGNETIC RESONANCE IMAGING APPARATUS

CROSS REFERENCE

This is a continuation of Application PCT/JP2012/62715, filed May 17, 2012.

This application is based upon and claims the benefit of priority from Japanese Patent Application No. 2011-114229, filed May 20, 2011; the entire contents of which are incorporated herein by reference.

FIELD

Embodiments described herein relate generally to a MRI (magnetic resonance imaging) apparatus.

BACKGROUND

The MRI apparatus is an image diagnostic apparatus which magnetically excites nuclear spins of a subject set in a static magnetic field with a RF (radio frequency) signals having the Larmor frequency and reconstructs an image based on NMR (nuclear magnetic resonance) signals generated due to the excitation.

The MRI apparatus includes a cylindrical WB (whole body) coil as a transmission RF coil which applies RF pulses to the whole imaging region. The WB coil is fixed to the gantry and it is not assumed that a user removes the WB coil. On the other hand, a local transmission RF coil which transmits RF pulses to a desired and restricted imaging region locally can be used for imaging. When a local transmission RF coil is used, the power consumption can be reduced and an RF magnetic field having a larger intensity can be generated with little electric power.

The local transmission RF coil is sent in the gantry with a subject in the state where the local transmission RF coil has been attached to the subject set on the bed. Thus, the local transmission RF coil is connected with the control system of the MRI apparatus via a connector. Then, the local transmission RF coil is used in the state where the local transmission RF coil has been arranged inside the WB coil.

In many MRI apparatuses, it is recognized by connecting a local transmission RF coil to a connector in an MRI apparatus side so that the local transmission RF coil can be used. Furthermore, the WB coil which is an RF coil for transmission is electrically broken when a connection of a local transmission RF coil is recognized by the system of an MRI apparatus side. Thereby, electric coupling between the local transmission RF coil and the WB coil is avoided.

Note that, many local transmission RF coils also have the function to receive NMR signals. Examples of local transmission/reception RF coil having the reception and transmission function of signals include a local transmission/reception RF coil for head and a local transmission/reception RF coil for knee. As a typical local transmission RF coil, a birdcage type of RF coil is known. The birdcage type of RF coil is a coil which is made by connecting two rings by rungs.

PRIOR TECHNICAL LITERATURE

Patent Literature 1 JPA 2009-142646

The conventional local transmission RF coil is not recognized by the system in the MRI apparatus side unless the connector of the local transmission RF coil side is connected to the connector of the MRI apparatus side. Therefore, if a local transmission RF coil whose connector is not connected to the connector of the MRI apparatus side is left in the gantry, RF pulses are to be transmitted from the WB coil in the state where the local transmission RF coil has been arranged in the WB coil.

The transmission frequency of a local transmission RF coil is adjusted to be same as that of the WB coil. For this reason, electric coupling arises between the local transmission RF coil and the WB coil. As a result, if an RF pulse is transmitted from the WB coil in the state where a local transmission RF coil has been arranged in the WB coil, a remarkably large induced electromotive force is generated in the local transmission RF coil. When a large induced electromotive force is generated in the local transmission RF coil and an induced current flows in the local transmission RF coil, the local transmission RF coil generates heat. Consequently, not only the local transmission RF coil may be damaged but harm, such as a burn, may occur to a patient.

It may actually happen for an operator of an MRI apparatus to forget connection of a connector, in spite of having set a local transmission RF coil in the gantry. Therefore, it is desired to develop a technology of avoiding breakage of a local transmission RF coil and ensuring the safety of a subject even in a case where an RF pulse has been accidentally transmitted with setting the local transmission RF coil in the gantry.

It is an object of the present invention to provide a magnetic resonance imaging apparatus which can avoid breakage of local transmission RF coils of RF pulses and ensure the safety of a subject even in a case where an unconnected local transmission RF coil has been left in the gantry and RF pulses have been applied to the WB coil.

DETAILED DESCRIPTION

In general, according to one embodiment, a magnetic resonance imaging apparatus includes a data acquisition system and a control system. The data acquisition system is configured to acquire magnetic resonance signals from a subject by applying a static magnetic field, a gradient magnetic field and a radio frequency magnetic field to an imaging area in which the subject is set. The control system is configured to acquire the magnetic resonance signals by controlling the data acquisition system to generate image data based on the acquired magnetic resonance signals. The data acquisition system has a whole body coil, a radio frequency coil and a breaker circuit. The whole body coil is configured to apply the radio frequency magnetic field to the imaging area. The radio frequency coil is configured to apply the radio frequency magnetic field to the imaging area when a radio frequency pulse has been applied from the control system through a connector. The radio frequency coil is set inside the whole body coil. The breaker circuit is configured to electrically break a part of a circuit constituting the radio frequency coil when the connector of the radio frequency coil has been disconnected to the control system. The breaker circuit has a coaxial cable and a short circuit. One end of the coaxial cable is connected with the part of the circuit constituting the radio frequency coil while another end is connected to the connector of the radio frequency coil. The part is a broken target. The short circuit is configured to be connected with the other end of the coaxial cable through the connector to electrically connect a central conductor of the coaxial cable with an external conductor when the connector of the radio frequency coil has been connected to the control system.

A magnetic resonance imaging apparatus according to an embodiment of the present invention will be described with reference to the accompanying drawings.

Figure 1:
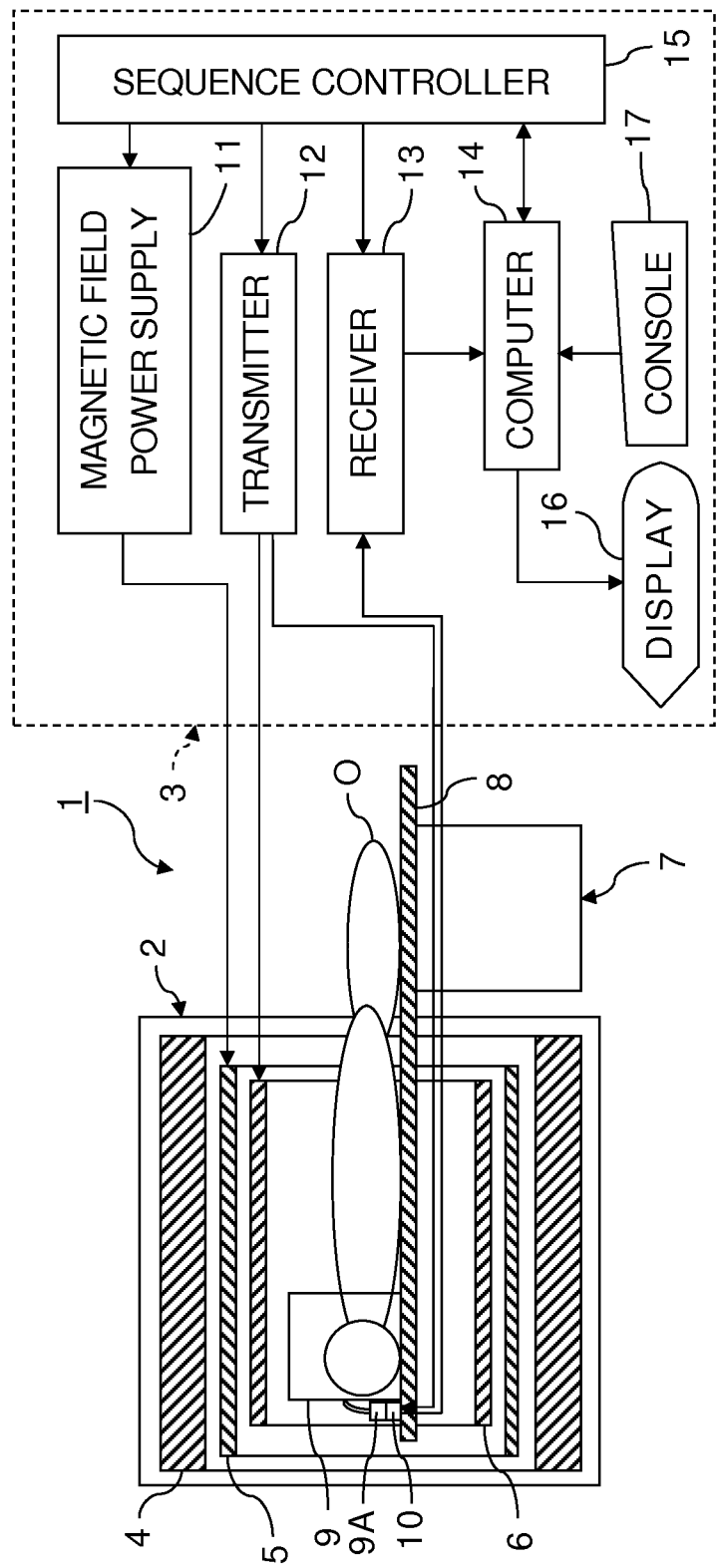
FIG. 1 is a block diagram showing a magnetic resonance imaging apparatus according to an embodiment of the present invention.

FIG. 1 is a block diagram showing a magnetic resonance imaging apparatus according to an embodiment of the present invention.

A magnetic resonance imaging apparatus 1 has the gantry 2 and the control system 3. The gantry 2 forms an imaging area. A cylindrical static magnetic field magnet 4 forming a static magnetic field in the imaging area, a cylindrical gradient coil 5 forming a gradient magnetic field in the imaging area, and a cylindrical WB coil 6 transmitting RF magnetic field pulses in the whole imaging area are coaxially built in the gantry 2. Moreover, a bed 7 is placed near the gantry 2. Then, a subject O can be sent into the imaging area in the gantry 2 together with a table 8 of the bed 7 in the state where the subject O has been set on the table 8.

Moreover, a local RF coil 9 can be set to the subject O inside the WB coil 6. Then, the local RF coil 9 can be used as a coil for transmission of RF magnetic field pulses. A coil connector 9A is provided with the local RF coil 9. When the local RF coil 9 is used, the coil connector 9A of the local RF coil 9 is connected with a system connector 10 in the MRI apparatus side. FIG. 1 shows an example of arranging the system connector 10, in the MRI apparatus side, on the table 8 of the bed 7 and connecting the local RF coil 9 for head to the MRI apparatus through the coil connector 9A and the system connector 10. As a typical local coil, a birdcage type coil is known.

The local RF coil 9 may be a coil which also has the reception function of NMR signals arising in the subject O. FIG. 1 shows an example where the local coil is a coil having the functions to transmit an RF pulse and receive an NMR signal. Note that, a phased array coil (PAC) having coil elements for reception of NMR signals or a local RF coil for reception of NMR signals may be arranged near an imaging part of the subject O aside from the local RF coil 9. Moreover, the WB coil 6 may be used as an RF reception coil.

Thus, the hardware including the static magnetic field magnet 4, the gradient coil 5 and the WB coil 6 respectively built in the gantry 2, and the local RF coil 9 set near the gantry 2 forms a data acquisition system for applying the static magnetic field, the gradient magnetic fields, and the RF magnetic fields in the imaging area, in which a subject O has been set, to acquire NMR signals from the subject O.

On the other hand, the control system 3 is a system which acquires NMR signals from the subject O and generates MR image data based on the acquired NMR signals by controlling the data acquisition system. Specifically, the control system 3 includes a gradient power supply 11, a transmitter 12, a receiver 13, a computer 14, a sequence controller 15, a display 16, and a console 17.

The gradient power supply 11 is a drive circuit for controlling the gradient coil 5 by applying a control pulse to the gradient coil 5. That is, the gradient power supply 11 has a function to allow the gradient coil 5 to apply gradient magnetic field pulses toward an imaging part of the subject O.

The transmitter 12 is a circuit to transmit RF pulses to the local RF coil 9 or the WB coil 6 so that RF magnetic fields are applied toward the subject O from the RF coil for transmission. For that purpose, the output side of the transmitter 12 branches. One end of the transmitter 12 is connected with the WB coil 6 and the system connector 10 is connected to the other end.

When the coil connector 9A of the local RF coil 9 has been connected to the system connector 10, the transmitter 12 is configured to recognize the connection of the local RF coil 9 and transmit RF pulses to the local RF coil 9. On the other hand, when the coil connector 9A of the local RF coil 9 has not been connected to the system connector 10, the transmitter 12 is configured to transmit RF pulses to the WB coil 6.

The receiver 13 is a circuit to receive NMR signals from RF reception coils and generate NMR data consisting of digital signals by signal processing including amplification, detection, and A/D (analog to digital) conversion. In FIG. 1, the local RF coil 9 serves as the RF reception coil. Therefore, the receiver 13 is connected with the output side of the local RF coil 9 through the coil connector 9A and the system connector 10 common for transmission of RF pulses.

The sequence controller 15 is a control circuit which drives the gradient power supply 11, the transmitter 12, and the receiver 13 according to imaging conditions including a pulse sequence output from the computer 14.

The computer 14 is controlled according to instructions input from the console 17 having an input device. The computer 14 has a function to generate MR image data by image reconstruction processing and necessary image processing of NMR signals, which are complex signals, acquired from the receiver 13 and a function to display the generated MR image data on the display 16.

Next, a more concrete function and a circuit configuration of the local RF coil 9 will be described. Here, a case where the local RF coil 9 is a birdcage type of local RF coil for transmission and reception having the function to transmit RF pulses and the function to receive NMR signals is explained as an example.

The local RF coil 9 is configured so as to be attached to and detached from each of the transmitter 12 and the receiver 13 of the control system 3 through the system connector 10 and the coil connector 9A. Then, the local RF coil 9 has a function to transmit an RF magnetic field pulse in a local imaging area when a RF pulse is applied from the transmitter 12 through the system connector 10 and the coil connector 9A in the state where the local RF coil 9 has been connected with each of the transmitter 12 and the receiver 13 of the control system 3 through the system connector 10 and the coil connector 9A. The local RF coil 9 also has a function to receive NMR signals from a subject O and output the received NMR signals to the receiver 13 through the system connector 10 and the coil connector 9A.

Moreover, the local RF coil 9 is provided with a breaker circuit which electrically breaks a part of circuit composing the local RF coil 9 when the coil connector 9A of the local RF coil 9 has not been connected to the system connector 10 of the control system 3 side. That is, the breaker circuit functions as a switch circuit which electrically switches a part of the circuit composing the local RF coil 9, between the connected state and the disconnected state, according to whether the coil connector 9A of the local RF coil 9 is connected to the system connector 10 of the control system 3 side or not.

Figure 2:
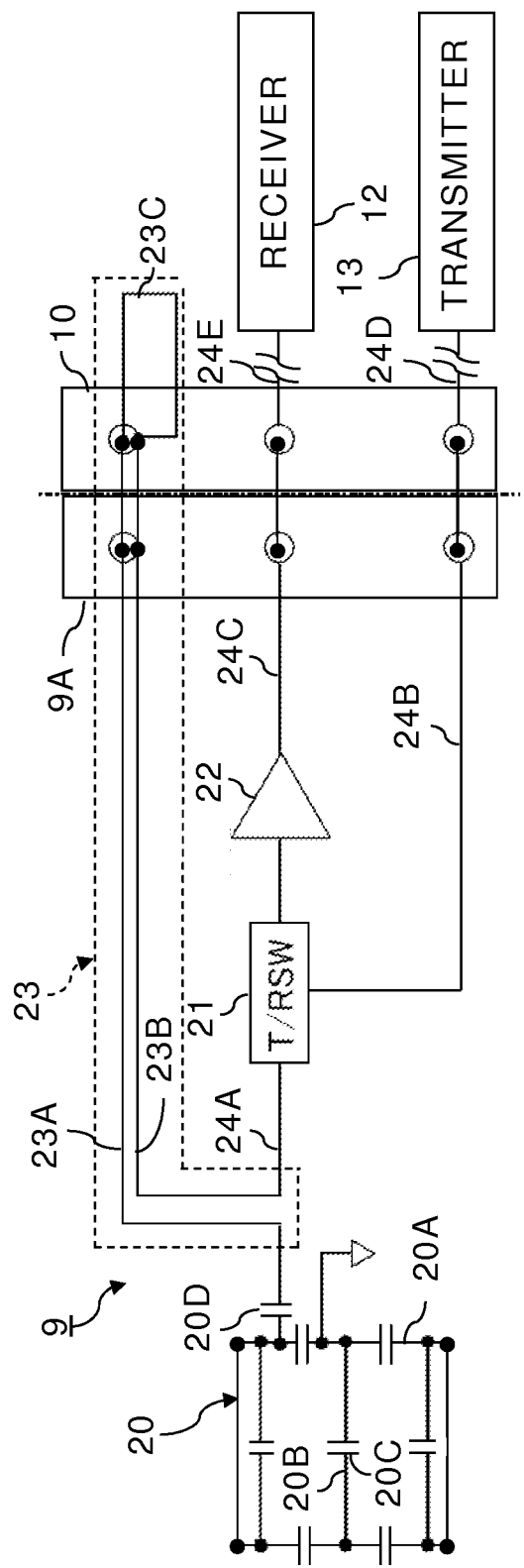
FIG. 2 is a view showing the first example of circuit configuration of the local RF coil shown in FIG. 1.
Figure 3:
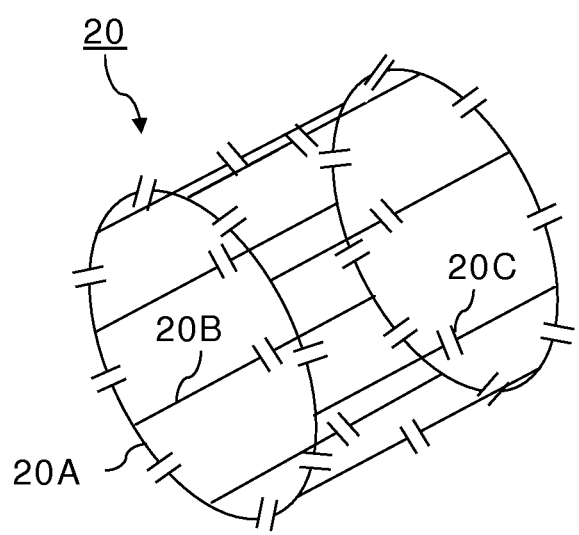
FIG. 3 is a perspective view showing an example of circuit configuration of coil element of a birdcage type RF coil used as the local RF coil shown in FIG. 1.

FIG. 2 is a view showing the first example of circuit configuration of the local RF coil 9 shown in FIG. 1. Moreover, FIG. 3 is a perspective view showing an example of circuit configuration of coil element of a birdcage type RF coil used as the local RF coil 9 shown in FIG. 1.

As shown by an example in FIG. 2, the local RF coil 9 has a coil element 20, a transmission/reception switching (T/R SW) circuit 21, a preamplifier 22, and the coil connector 9A. The coil element 20 is connected with the transmission/reception switching circuit 21 by a signal line 24A, common to transmission and reception, through a breaker circuit 23.

Moreover, one end of each of a signal line 24B for transmission of RF transmission pulses in the local RF coil 9 side and a signal line 24C for transmission of NMR signals is connected to the transmission/reception switching circuit 21. Meanwhile, the other end of each of the signal line 24B for transmission of RF transmission pulses and the signal line 24C for transmission of NMR signals is connected with the coil connector 9A. Furthermore, the preamplifier 22 is connected to the signal line 24C, for transmission of NMR signals, between the transmission/reception switching circuit 21 and the coil connector 9A.

On the other hand, one end of each of a signal line 24D for transmission of RF transmission pulses and a signal line 24E for transmission of NMR signals in the control system 3 side is connected to the system connector 10. Then, the other end of the signal line 24D for transmission of RF transmission pulses is connected with the transmitter 12 while the other end of the signal line 24E for transmission of NMR signals is connected with the receiver 13.

The coil element 20 is a coil which transmits RF pulses toward a subject O set in the imaging area and receives NMR signals arising from the subject O. The birdcage-shaped coil element 20 is made by connecting one of two end rings 20A with the other by rungs 20B as shown in FIG. 2 and FIG. 3. Each end ring 20A and each rung 20B includes respectively corresponding conductors. Further condenser elements 20C are connected to predetermined positions of one or both of the end rings 20A and the rungs 20B, for the frequency adjustment of the coil element 20.

Furthermore, a matching condenser 20D as a circuit for matching impedance is connected to the coil element 20 through the signal line 24A common to transmission and reception. Usually, a variable condenser element is used for the matching condenser 20D.

The transmission/reception switching circuit 21 is a switch circuit which switches the signal path of RF transmission pulses from the transmitter 12 toward the coil element 20 and the signal path of NMR reception signals from the coil element 20 toward the receiver 13.

The coil connector 9A has a shape which fits the system connector 10 of the control system 3 side so that the coil connector 9A is attachable and detachable to the system connector 10. Thus, the coil connector 9A is configured to be connected with the system connector 10 of the control system 3 side so that the signal line 24B for transmission of RF transmission pulses in the local RF coil 9 side is connected with the signal line 24D for transmission of RF transmission pulses of the control system 3 side while the signal line 24C for transmission of NMR signals in the local RF coil 9 side is connected with the signal line 24E for transmission of NMR signals of the control system 3 side.

The preamplifier 22 is an amplifier which amplifies NMR signals output from the coil element 20 through the breaker circuit 23 and the transmission/reception switching circuit 21, and outputs the amplified NMR signals to the receiver 13 through the coil connector 9A and the system connector 10.

The breaker circuit 23 is connected between the coil element 20 and the transmission/reception switching circuit 21 as mentioned above. More specifically, the breaker circuit 23 is connected between the matching condenser 20D and the transmission/reception switching circuit 21. The breaker circuit 23 is a circuit which electrically breaks between the coil element 20 and the transmission/reception switching circuit 21 when the coil connector 9A of the local RF coil 9 has been not connected to the system connector 10 in the control system 3 side. For that purpose, the breaker circuit 23 has the first signal line 23A, the second signal line 23B, and a short circuit 23C.

One end of the first signal line 23A is connected with the signal line 24A, common to transmission and reception, connected to the coil element 20 side. Alternatively, the first signal line 23A is the signal line 24A itself, common to transmission and reception, connected to the coil element 20 side. On the other hand, one end of the second signal line 23B is connected with the signal line 24A, common to transmission and reception, connected to the transmission/reception switching circuit 21 side. Alternatively, the second signal line 23B is the signal line 24A itself, common to transmission and reception, connected to the transmission/reception switching circuit 21 side. Each other end of the first signal line 23A and the second signal line 23B is connected with the coil connector 9A respectively in the state where one of the ends is not electrically connected with the other.

The short circuit 23C is connected with the system connector 10 in the control system 3 side. The short circuit 23C is the circuit having a signal line which electrically connects the first signal line 23A with the second signal line 23B in the control system 3 side. By the short circuit 23C, the coil element 20 is electrically connected with the transmission/reception switching circuit 21 through the coil connector 9A and the system connector 10.

According to the breaker circuit 23 which has such a circuit configuration, the coil element 20 is electrically connected with the transmission/reception switching circuit 21 by the signal pass via the first signal line 23A, the short circuit 23C, and the second signal line 23B under the state where the coil connector 9A has been connected with the system connector 10. On the other hand, under the state where the coil connector 9A has not been connected with the system connector 10, the first signal line 23A is not electrically connected with the second signal line 23B. Therefore, the coil element 20 is electrically shut off from the transmission/reception switching circuit 21. As a result, the resonance frequency of the local RF coil 9 changes to be detuned from the frequency of RF transmission pulses.

Therefore, even if an RF transmission pulse is applied to the WB coil 6 from the transmitter 12 in the state where the coil connector 9A of the local RF coil 9 placed inside the WB coil 6 has not been connected to the system connector 10, an induced current which arises in the coil element 20 can be reduced sufficiently. Moreover, even if an induced current should arise in the coil element 20, it can be avoided that the induced current flows into circuits, such as the transmission/reception switching circuit 21, the preamplifier 22, the transmitter 12, and the receiver 13.

Note that, a part or all of the first signal line 23A and the second signal line 23B may also be made by coaxial cables. In this case, one end of the coaxial cable is connected with the signal line 24A, to be a broken target, between the coil element 20 and transmission/reception switching circuit 21, and the other end is connected with the coil connector 9A.

That is, one end of the central conductor of the coaxial cable is connected with the coil element 20 while one end of the external conductor (shield conductor) is connected with the transmission/reception switching circuit 21. Alternatively, one end of the external conductor of the coaxial cable is connected with the coil element 20 while one end of the central conductor is connected with the transmission/reception switching circuit 21, on the contrary. Then, the other end of each of the central conductor and the external conductor of the coaxial cable is connected with the coil connector 9A in the state where one of the central conductor and the external conductor is not electrically connected with the other.

In this case, the short circuit 23C is connected with one end of the coaxial cable through the coil connector 9A and the system connector 10 when the other end of the coil connector 9A is connected to the other end of the system connector 10. Then, the short circuit 23C becomes a circuit having a signal line which electrically connects the central conductor of the coaxial cable with the external conductor.

However, if the length l of the coaxial cable has the relation defined by the formula (1) in the state where the central conductor has been electrically connected with the external conductor in one end of the coaxial cable, the central conductor shorts with the external conductor in the other end.

$$l = n\lambda/2 \quad (1)$$

wherein n is a natural number, and 2, is a wavelength of an alternating current which flows through the coaxial cable.

When the central conductor has been electrically connected with the external conductor in one end of the coaxial cable, the condition for electrically disconnecting the central conductor from the external conductor in the other end is that the length l of the coaxial cable satisfies the relation of the formula (2)

$$l = n\lambda/2 + \lambda/4 \quad (2)$$

Therefore, when a coaxial cable is used as the first signal line 23A and the second signal line 23B in FIG. 2, it is optimal to determine the length l of the coaxial cable so as to satisfy the formula (1).

Note that, in case of electrically disconnecting the central conductor in one end of the coaxial cable with the external conductor, the formula (1) is the condition to electrically disconnect the central conductor in the other end of the coaxial cable with the external conductor while the formula (2) is the condition to short the central conductor in the other end of the coaxial cable with the external conductor.

In the first example of circuit configuration of the local RF coil 9 shown in FIG. 2, the breaker circuit 23 is configured to break between the coil element 20 and the transmission/reception switching circuit 21. However, the breaker circuit 23 may also be configured to break at least one of a condenser element 20C and a conductor, which constitute the local RF coil 9, from the local RF coil 9.

If a coaxial cable and the short circuit 23C, which shorts one end of the coaxial cable in the control system 3 side, are used as elements of the breaker circuit 23, a desired portion can be electrically broken from the local RF coil 9 by connecting one end of the coaxial cable with a part of a circuit, such as a condenser element 20C or a conductor, to be a broken target while connecting the other end with the coil connector 9A.

Figure 4:
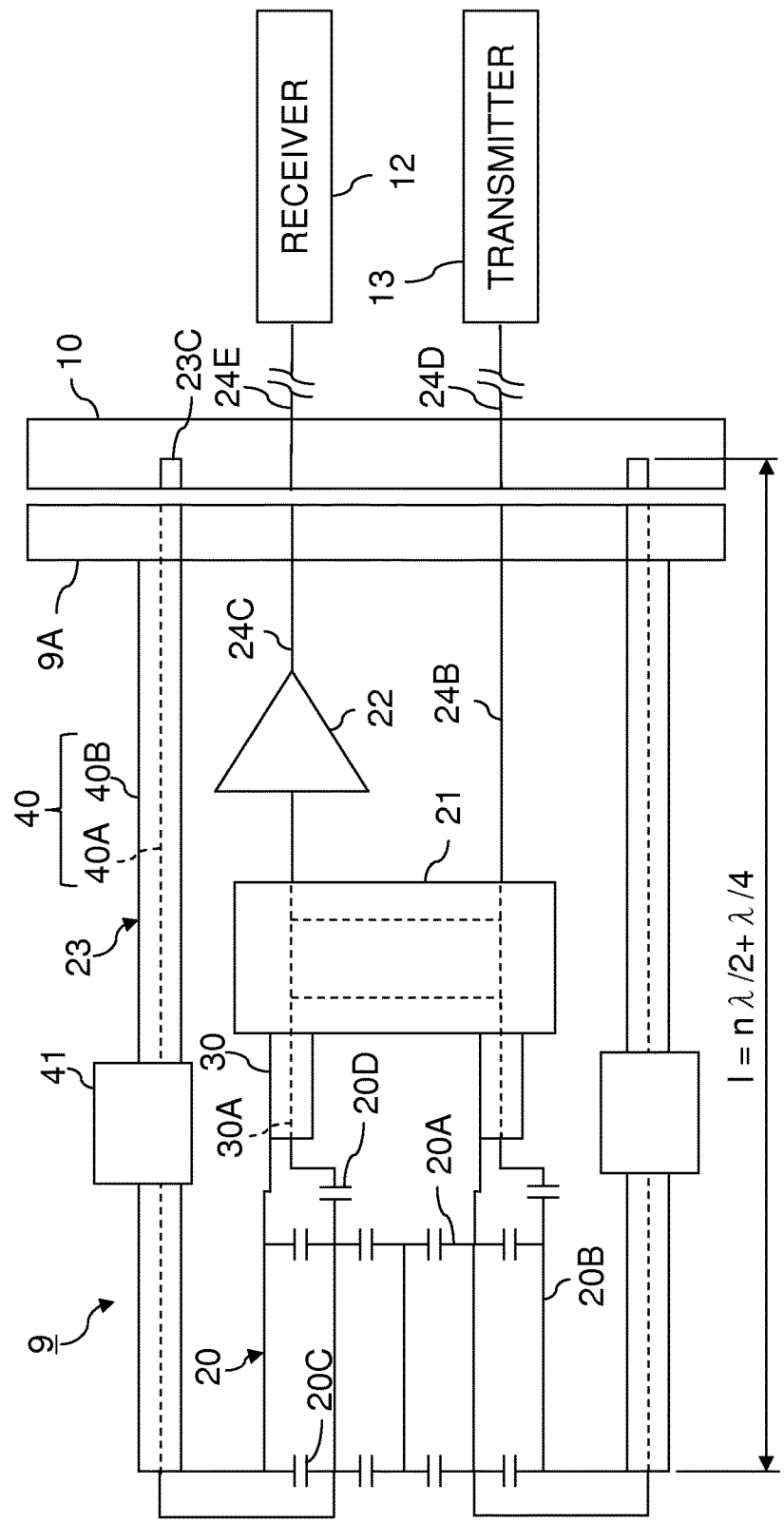
FIG. 4 is a view showing the second example of circuit configuration of the local RF coil shown in FIG. 1.

FIG. 4 is a view showing the second example of circuit configuration of the local RF coil 9 shown in FIG. 1.

The local RF coil 9 having the second example of circuit configuration shown in FIG. 4 has the coil element 20, the transmission/reception switching circuit 21, the preamplifier 22, and the coil connector 9A like the local RF coil 9 illustrated in FIG. 2. However, in the local RF coil 9 shown in FIG. 4, a 90-degree hybrid is used as the transmission/reception switching circuit 21. The 90-degree hybrid is a circuit which distributes an input signal into signals having phases mutually different by 90 degrees to output the distributed signals.

Moreover, in the example of FIG. 4, a birdcage type coil in which the condenser elements 20C are connected to the end rings 20A is used as the coil element 20. The coil element 20 is connected with the transmission/reception switching circuit 21 through two ports by two coaxial cables 30. Furthermore, a matching condenser 20D for an impedance matching is connected between a central conductor 30A of each coaxial cable 30 and the coil element 20.

On the other hand, the breaker circuit 23 has coaxial cables 40 and the short circuits 23C. FIG. 4 shows an example of connecting the two breaker circuits 23 with the local RF coil 9. That is, two sets each having the coaxial cable 4 and the short circuit 23C are connected to the local RF coil 9.

Each breaker circuit 23 is connected with a condenser element 20C of the coil element 20 which is a target broken from the local RF coil 9 in case where the coil connector 9A has not been connected to the system connector 10 in the control system 3 side. Specifically, one end of each coaxial cable 40 is connected with the both ends of a condenser element 20C. That is, the central conductor 40A of each coaxial cable 40 is connected with one end of a condenser element 20C while the external conductor 40B of each coaxial cable 40 is connected with the other end of the condenser element 20C.

The other end of each coaxial cable 40 is connected with the coil connector 9A in the state where the central conductor 40A is not electrically connected with the external conductor 40B. In addition, a balun (balance-unbalance converter) 41 is connected to each coaxial cable 40.

On the other hand, each short circuit 23C is connected with the system connector 10 in the control system 3 side. That is, each short circuit 23C is connected with the other end of the corresponding coaxial cable 40, through the coil connector 9A and the system connector 10, in the control system 3 side. Each short circuit 23C is the circuit having a signal line which electrically connects the central conductor 40A of the corresponding coaxial cable 40 with the external conductor 40B.

Then, the length l of each coaxial cable 40 is determined so as to satisfy the formula (2). Namely, the length l of each coaxial cable 40 is determined so that the central conductor 40A of each coaxial cable 40 is electrically disconnected from the external conductor 40B in the local RF coil 9 side when the coil connector 9A has been connected with the system connector 10 in the control system 3 side and the central conductor 40A of each coaxial cable 40 has shorted with the external conductor 40B in the control system 3 side by the short circuit 23C.

According to the breaker circuit 23 which has the above-mentioned circuit configuration, when the coil connector 9A of the local RF coil 9 has not been connected to the system connector 10 in the control system 3 side, the central conductors 40A of the coaxial cables 40 do not short with the external conductors 40B respectively in the control system 3 side. Therefore, the central conductors 40A of the coaxial cables 40 short with the external conductors 40B respectively. As a result, the both ends of each condenser element 20C of the coil element 20 to which the coaxial cable 40 is connected become the shorted state, and the resonance frequency of the coil element 20 is detuned from the frequency of RF transmission pulses applied to the WB coil 6.

On the contrary, when the coil connector 9A of the local RF coil 9 has been connected to the system connector 10 in the control system 3 side, the central conductors 40A of the coaxial cables 40 short with the external conductors 40B respectively in the control system 3 side by the short circuits 23C. Meanwhile, the central conductors 40A and the external conductors 40B of the coaxial cables 40 become the disconnected state in the coil element 20 side. As a result, the both ends of each condenser element 20C of the coil element 20, to which the coaxial cable 40 has been connected, have a high impedance, and the condenser elements 20C contribute to adjustment of the resonance frequency of the local RF coil 9. That is, the resonance frequency of the local RF coil 9 can be tuned up to the frequency of RF transmission pulses so that the local RF coil 9 can be used for an imaging.

Note that, from a viewpoint of sufficiently changing the resonance frequency of the local RF coil 9 from the frequency of RF transmission pulses when the coil connector 9A has not been connected to the system connector 10, it is preferable to set the breaker circuits 23 for as many condenser elements 20C of the local RF coil 9 as possible. Therefore, it is considered that it is practically desirable to set the breaker circuits 23 for four or more condenser elements 20C although the example of connecting the breaker circuits 23 to the two condenser elements 20C respectively is shown in FIG. 4 for simplifying explanation.

Figure 5:
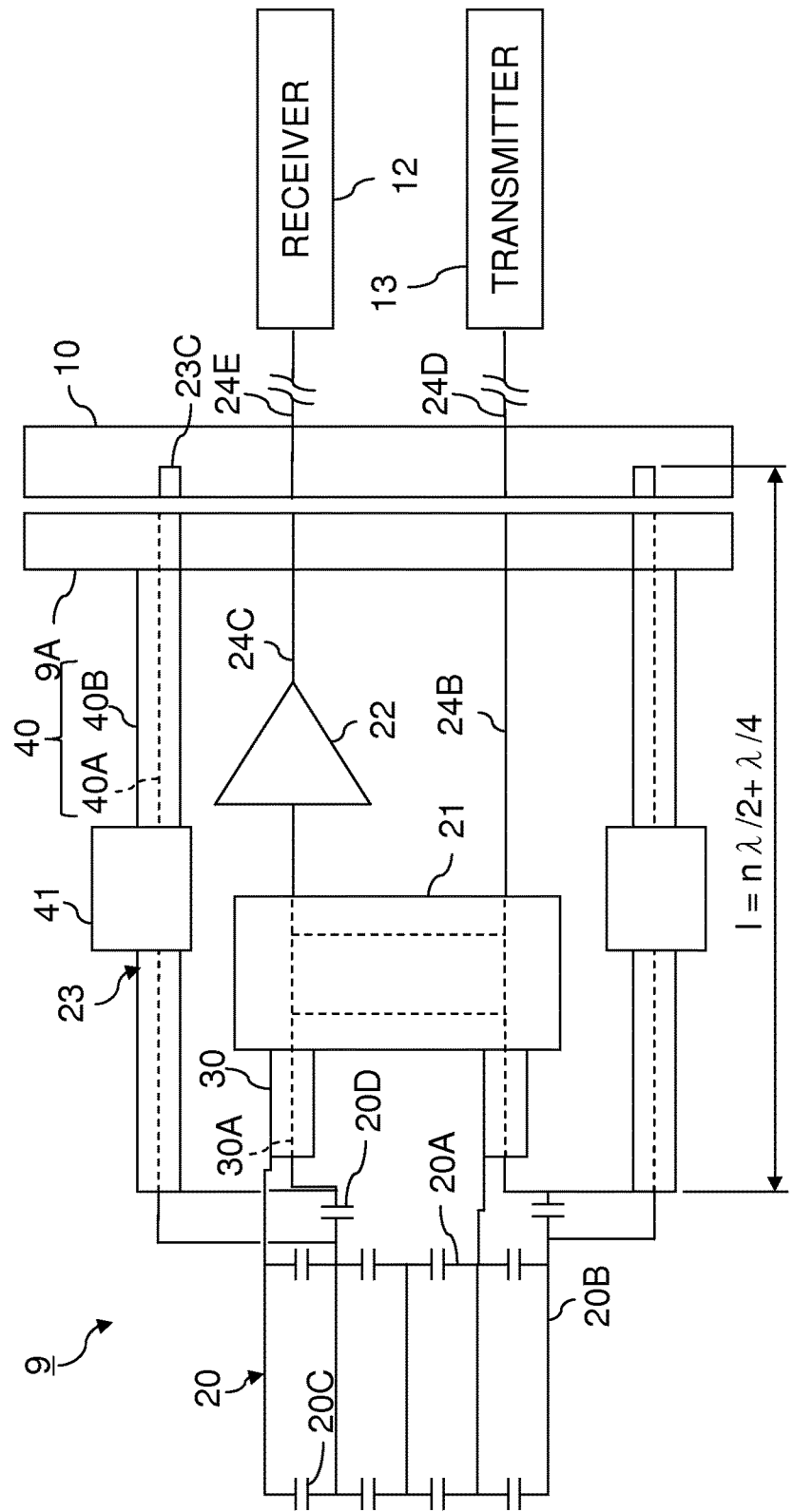
FIG. 5 is a view showing the third example of circuit configuration of the local RF coil shown in FIG. 1.

FIG. 5 is a view showing the third example of circuit configuration of the local RF coil 9 shown in FIG. 1.

The local RF coil 9 in the third example of circuit configuration shown in FIG. 5 has a circuit configuration similar to that of the local RF coil 9 in the second example of circuit configuration shown in FIG. 4. However, the breaker circuits 23 are connected to the matching condensers 20D respectively.

More specifically, the end part of each coaxial cable 40 in the coil element 20 side is connected to the both ends of the matching condenser 20D. That is, the central conductor 40A of each coaxial cable 40 in the coil element 20 side is connected to one end of the matching condenser 20D while the external conductor 40B is connected to the other end of the matching condenser 20D.

Then, the length l of each coaxial cable 40 is determined so as to satisfy the formula (2). That is, the third example of circuit configuration of the local RF coil 9 shown in FIG. 5 is one in which the matching condensers 20D connected to the coil element 20 are broken targets by the breaker circuits 23.

According to the breaker circuit 23 having the above-mentioned circuit configuration, when the coil connector 9A has not been connected to the system connector 10, the both ends of each matching condenser 20D become the shorted state by the breaker circuits 23. As a result, the resonance frequency of the local RF coil 9 can be detuned from the frequency of RF transmission pulses similarly to the local RF coil 9 in the second example of circuit configuration shown in FIG. 4.

Figure 6:
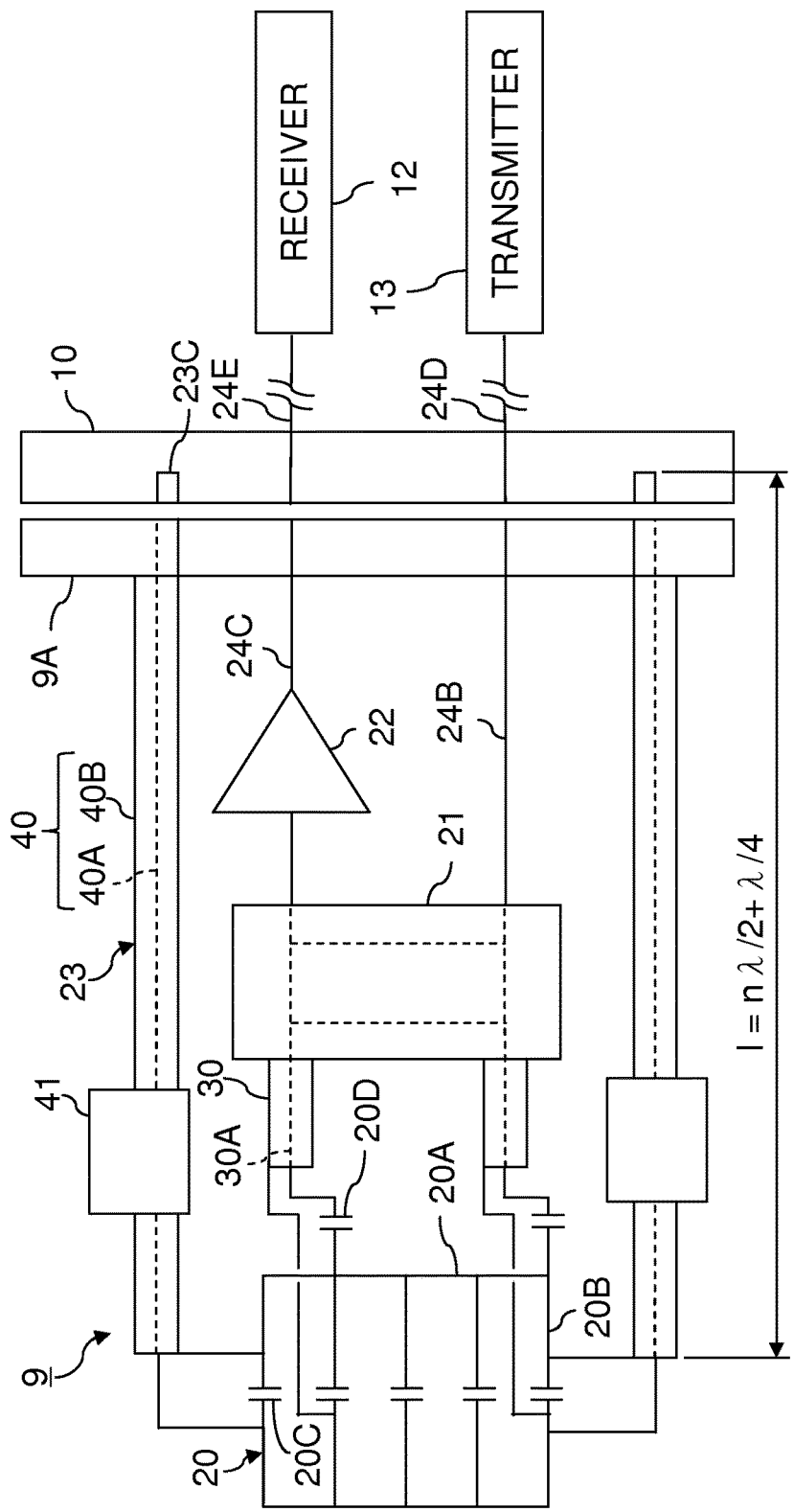
FIG. 6 is a view showing the fourth example of circuit configuration of the local RF coil shown in FIG. 1.

FIG. 6 is a view showing the fourth example of circuit configuration of the local RF coil 9 shown in FIG. 1.

The local RF coil 9 in the fourth example of circuit configuration shown in FIG. 6 has a circuit configuration similar to that of the local RF coil 9 in the second example of circuit configuration shown in FIG. 4. However, a birdcage type coil in which the condenser elements 20C are connected to the rungs 20B is used as the coil element 20.

Therefore, the breaker circuits 23 are connected to the condenser elements 20C set to the rungs 20B. More specifically, the end part of each coaxial cable 40 in the coil element 20 side is connected to the both ends of a condenser element 20C set to a rung 20B. That is, the central conductor 40A of each coaxial cable 40 in the coil element 20 side is connected to one end of a condenser element 20C set to a rung 20B while the external conductor 40B is connected to the other end of the condenser element 20C set to the rung 20B.

Then, the length l of each coaxial cable 40 is determined so as to satisfy the formula (2). That is, the fourth example of circuit configuration of the local RF coil 9 shown in FIG. 6 is one in which the condenser elements 20C connected to the rungs 20B of the coil element 20 are broken targets by the breaker circuits 23.

According to the breaker circuit 23 having the above-mentioned circuit configuration, when the coil connector 9A has not been connected to the system connector 10, the both ends of each of the condenser elements 20C connected to the rungs 20B become the shorted state by the breaker circuits 23. As a result, the resonance frequency of the local RF coil 9 can be detuned from the frequency of RF transmission pulses similarly to the local RF coil 9 in the second example of circuit configuration shown in FIG. 4.

Although the examples of respectively connecting the breaker circuits 23 to the condenser elements 20C which constitute the local RF coil 9 are shown in FIG. 4, FIG. 5, and FIG. 6, the breaker circuits 23 may be connected to portions other than the condenser elements 20C so long as the portions are elements contributing to the resonance frequency of the local RF coil 9.

Figure 7:
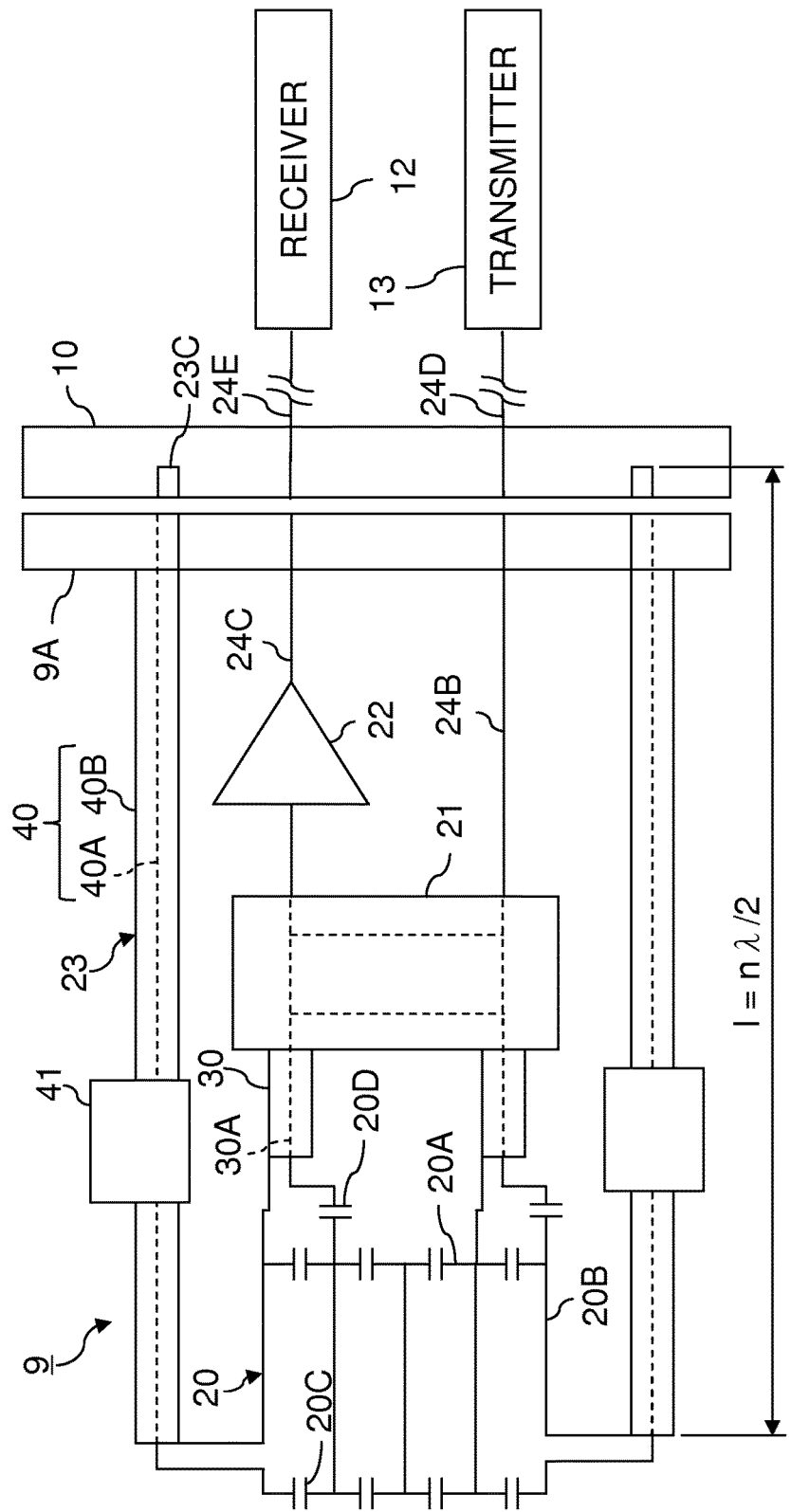
FIG. 7 is a view showing the fifth example of circuit configuration of the local RF coil shown in FIG. 1.

FIG. 7 is a view showing the fifth example of circuit configuration of the local RF coil 9 shown in FIG. 1.

The local RF coil 9 in the fifth example of circuit configuration shown in FIG. 7 has a circuit configuration similar to that of the local RF coil 9 illustrated in FIG. 4. However, the breaker circuits 23 are connected to rungs 20B which constitute conductors of the coil element 20. That is, the local RF coil 9 shown in FIG. 7 is one in which the rungs 20B of the coil element 20 are broken targets by the breaker circuits 23.

More specifically, the end part of each coaxial cable 40 in the coil element 20 side is connected to a rung 20B of the coil element 20. That is, rungs 20B are cut. Then, the central conductor 40A of each coaxial cable 40 in the coil element 20 side is connected to one end of the cut rung 20B while the external conductor 40B of each coaxial cable 40 in the coil element 20 side is connected to the other end of the cut rung 20B.

Then, the length l of each coaxial cable 40 is determined so as to satisfy the formula (1). Therefore, the central conductor 40A of each coaxial cable 40 does not short with the external conductor 40B in the control system 3 side when the coil connector 9A of the local RF coil 9 has not been connected to the system connector 10 in the control system 3 side. Hence, the central conductor 40A of each coaxial cable 40 does not also short with the external conductor 40B in the coil element 20 side. As a result, the rungs 20B each connected to the coaxial cable 40 have high impedances, and the resonance frequency of the coil element 20 is detuned from the frequency of RF transmission pulses applied to the WB coil 6.

On the contrary, when the coil connector 9A of the local RF coil 9 has been connected to the system connector 10 in the control system 3 side, the central conductor 40A of each coaxial cable 40 shorts with the external conductor 40B in the control system 3 side by the short circuit 23C. Therefore, the central conductor 40A and the external conductor 40B of each coaxial cable 40 also become the connected state in the coil element 20 side. As a result, the rungs 20B to which the coaxial cables 40 are connected function as conductors. That is, the local RF coil 9 in the state where the resonance frequency has been tuned up to the frequency of RF transmission pulses can be used for an imaging.

Figure 8:
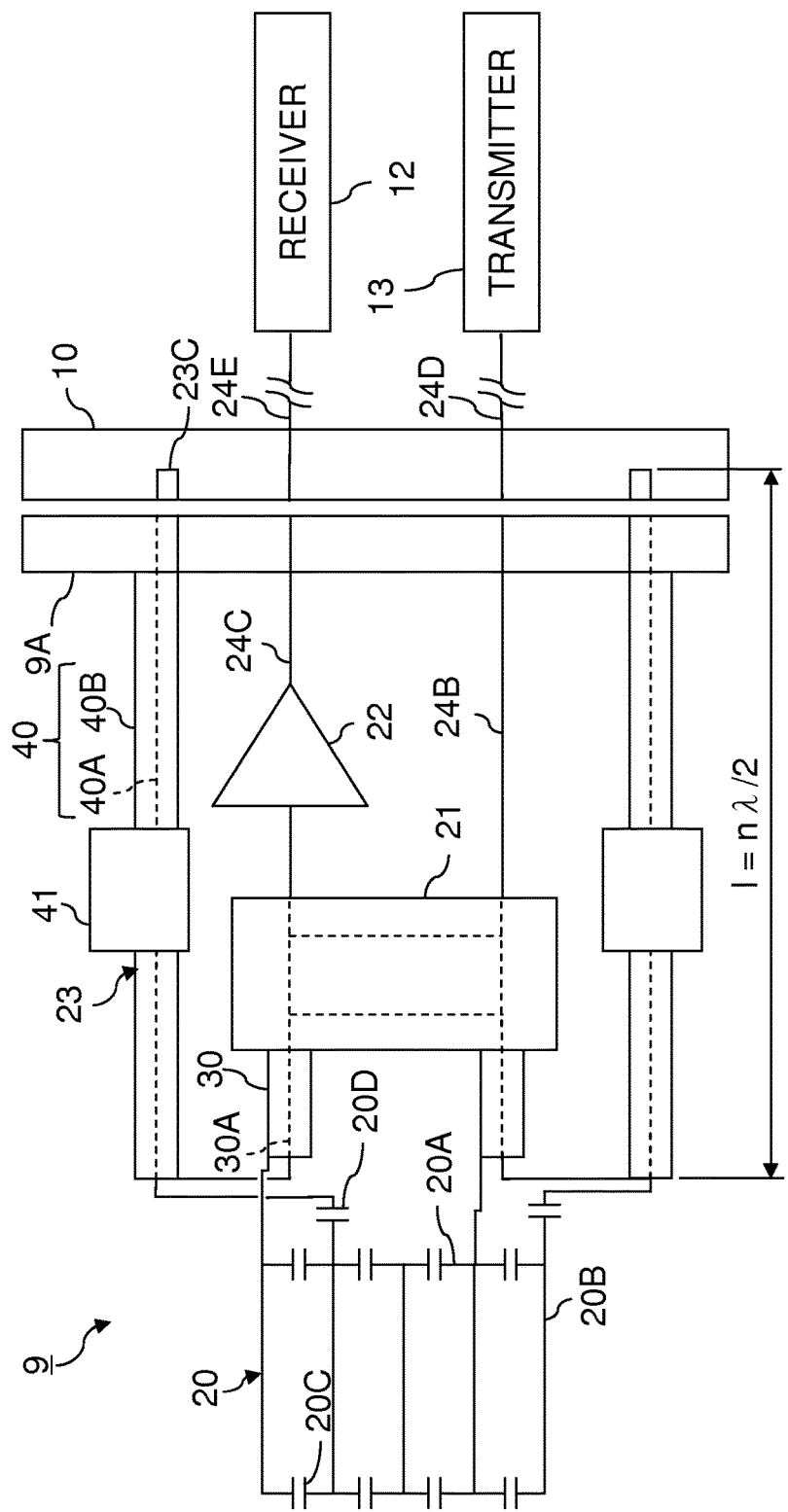
FIG. 8 is a view showing the sixth example of circuit configuration of the local RF coil shown in FIG. 1.

FIG. 8 is a view showing the sixth example of circuit configuration of the local RF coil 9 shown in FIG. 1.

The local RF coil 9 in the sixth example of circuit configuration shown in FIG. 8 has a circuit configuration similar to that of the local RF coil 9 illustrated in FIG. 7. However, the breaker circuits 23 are connected to the signal lines between the central conductors 30A of the coaxial cables 30 connected to the transmission/reception switching circuit 21 and the matching condensers 20D. That is, the local RF coil 9 shown in FIG. 8 is one in which the signal lines between the central conductors 30A of the coaxial cables 30 connected to the transmission/reception switching circuit 21 and the matching condensers 20D are broken targets by the breaker circuits 23.

More specifically, the end part of each of the coaxial cables 40 of the breaker circuits 23 in the coil element 20 side is connected to the signal line between the central conductor 30A of the coaxial cable 30 connected to the transmission/reception switching circuit 21 and the matching condenser 20D. Namely, the signal lines between the central conductors 30A of the coaxial cables 30 connected to the transmission/reception switching circuit 21 and the matching condensers 20D are cut respectively. Then, the central conductor 40A of the coaxial cable 40 of each breaker circuit 23 in the coil element 20 side is connected to one end of the cut signal line while the external conductor 40B of the coaxial cable 40 of each breaker circuit 23 in the coil element 20 side is connected to the other end of the cut signal line.

Then, the length l of each coaxial cable 40 is determined so as to satisfy the formula (1). Therefore, the signal lines between the central conductors 30A of the coaxial cables 30 connected to the transmission/reception switching circuit 21 and the matching condensers 20D are broken by the breaker circuits 23 when the coil connector 9A of the local RF coil 9 has not been connected to the system connector 10 in the control system 3 side. As a result, the resonance frequency of the local RF coil 9 can be detuned from the frequency of RF transmission pulses.

Figure 9:
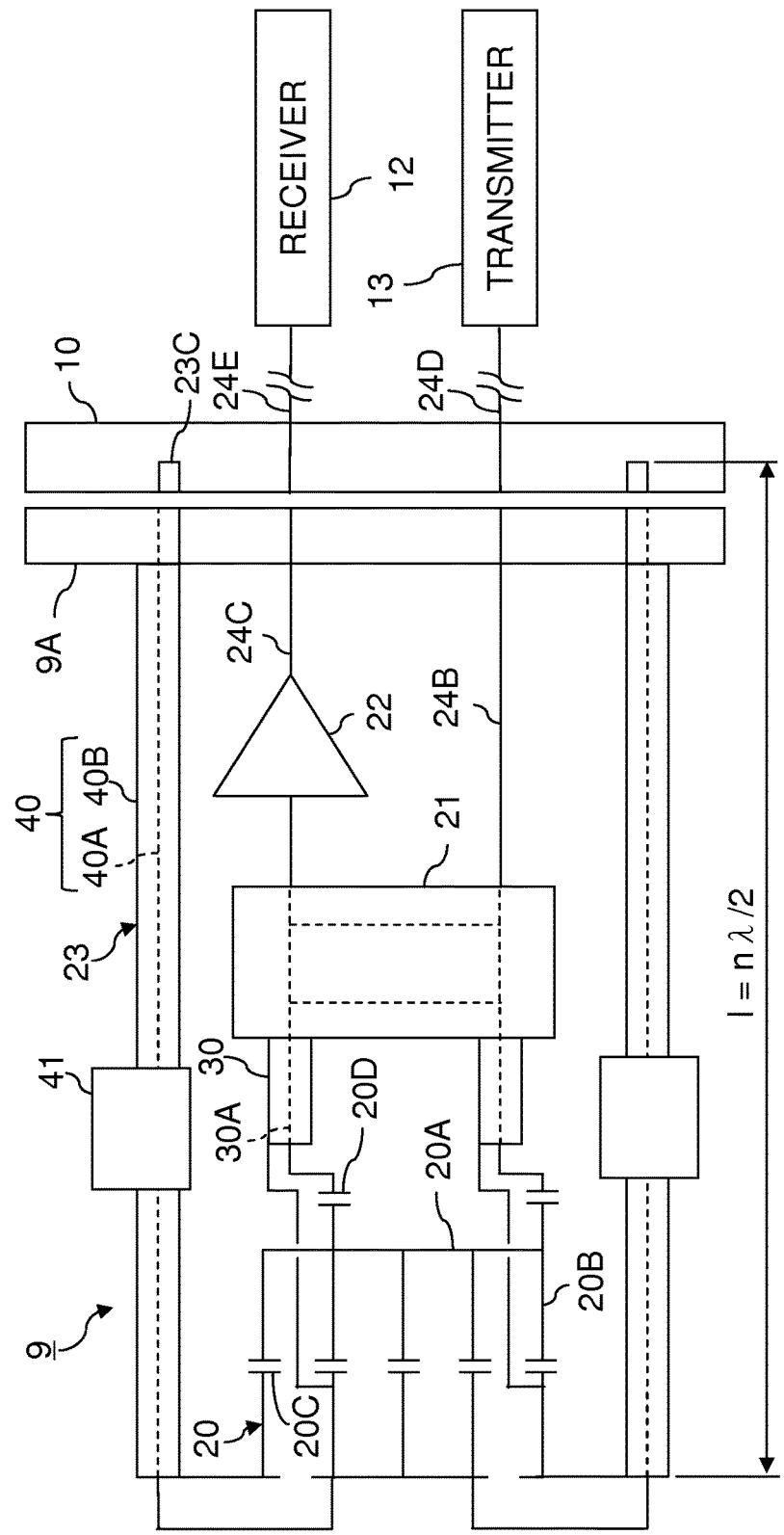
FIG. 9 is a view showing the seventh example of circuit configuration of the local RF coil shown in FIG. 1.

FIG. 9 is a view showing the seventh example of circuit configuration of the local RF coil 9 shown in FIG. 1.

The local RF coil 9 in the seventh example of circuit configuration shown in FIG. 9 has a circuit configuration similar to that of the local RF coil 9 illustrated in FIG. 7. However, a birdcage type coil in which the condenser elements 20C are connected to the rungs 20B is used as the coil element 20. In addition, the breaker circuits 23 are connected to an end ring 20A which constitutes a conductor of the coil element 20. That is, the local RF coil 9 shown in FIG. 9 is one in which the end ring 20A of the coil element 20 is a broken target by the breaker circuits 23.

More specifically, the end part of each coaxial cable 40 in the coil element 20 side is connected to the end ring 20A of the coil element 20. That is, the end ring 20A is cut. Then, the central conductor 40A of each coaxial cable 40 in the coil element 20 side is connected to one end of the cut end ring 20A while the external conductor 40B of each coaxial cable 40 in the coil element 20 side is connected to the other end of the cut end ring 20A.

Then, the length l of each coaxial cable 40 is determined so as to satisfy the formula (1). Therefore, the end ring 20A is cut by the breaker circuits 23 when the coil connector 9A of the local RF coil 9 has not been connected to the system connector 10 in the control system 3 side. As a result, the resonance frequency of the local RF coil 9 can be detuned from the frequency of RF transmission pulses.

Besides the above-mentioned examples of circuit configuration, a part of circuit which constitutes the local RF coil 9 can be also electrically broken from the local RF coil 9 by constituting a resonant circuit with the elements of the breaker circuit 23 and the elements other than the breaker circuit 23 of the local RF coil 9.

Figure 10:
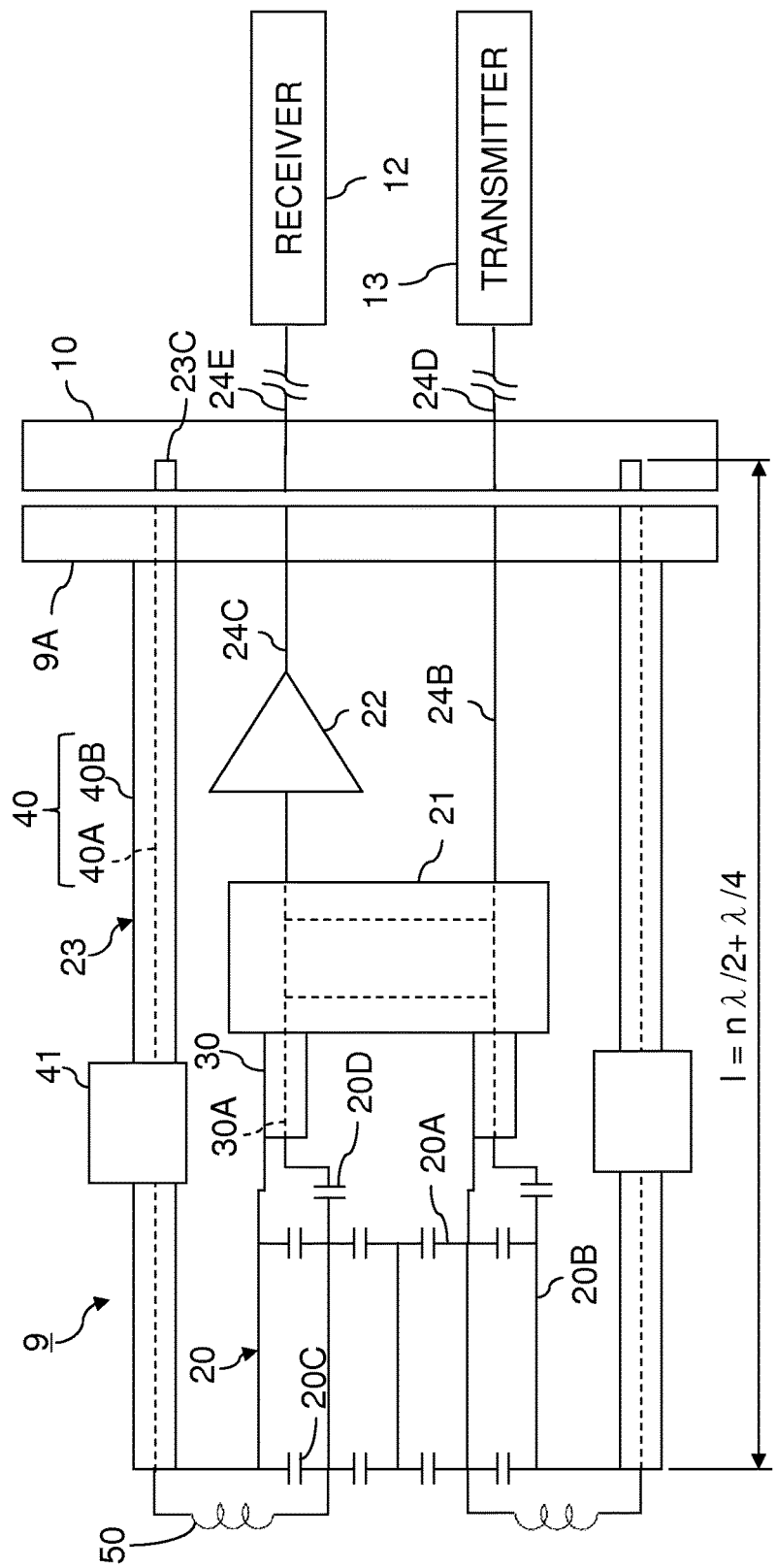
FIG. 10 is a view showing the eighth example of circuit configuration of the local RF coil shown in FIG. 1.

FIG. 10 is a view showing the eighth example of circuit configuration of the local RF coil 9 shown in FIG. 1.

The local RF coil 9 in the eighth example of circuit configuration shown in FIG. 10 has a circuit configuration similar to that of the local RF coil 9 in the second example of circuit configuration shown in FIG. 4. However, each breaker circuit 23 has an inductor 50. The inductors 50 are respectively connected between the condenser elements 20C to be broken targets and the central conductors 40A or the external conductors 40B in one ends of the coaxial cables 40. Furthermore, the inductances of the inductors 50 are determined according to the capacitances of the corresponding condenser elements 20C so that the inductors 50 resonate with the corresponding condenser elements 20C respectively.

Then, the length l of each coaxial cable 40 is determined so as to satisfy the formula (2). Therefore, when the coil connector 9A of the local RF coil 9 has not been connected to the system connector 10 in the control system 3 side, the central conductor 40A of each coaxial cable 40 shorts with the external conductor 40B in the coil element 20 side. As a result, a parallel resonant circuit is formed by the condenser element 20C and the inductor 50.

This parallel resonant circuit is equivalent to a switch circuit breaking a current. Therefore, the condenser element 20C to which the breaker circuit 23 has been connected does not contribute to adjustment of the resonance frequency of the local RF coil 9. Thereby, the resonance frequency of the local RF coil 9 can be detuned from the frequency of RF transmission pulses.

On the other hand, when the coil connector 9A of the local RF coil 9 has been connected to the system connector 10 in the control system 3 side, the central conductor 40A of each coaxial cable 40 does not short with the external conductor 40B in the coil element 20 side. Therefore, the inductors 50 do not influence the resonance frequency of the local RF coil 9. That is, the local RF coil 9 in the state where the resonance frequency has been tuned up to the frequency of RF transmission pulses can be used for an imaging.

Figure 11:
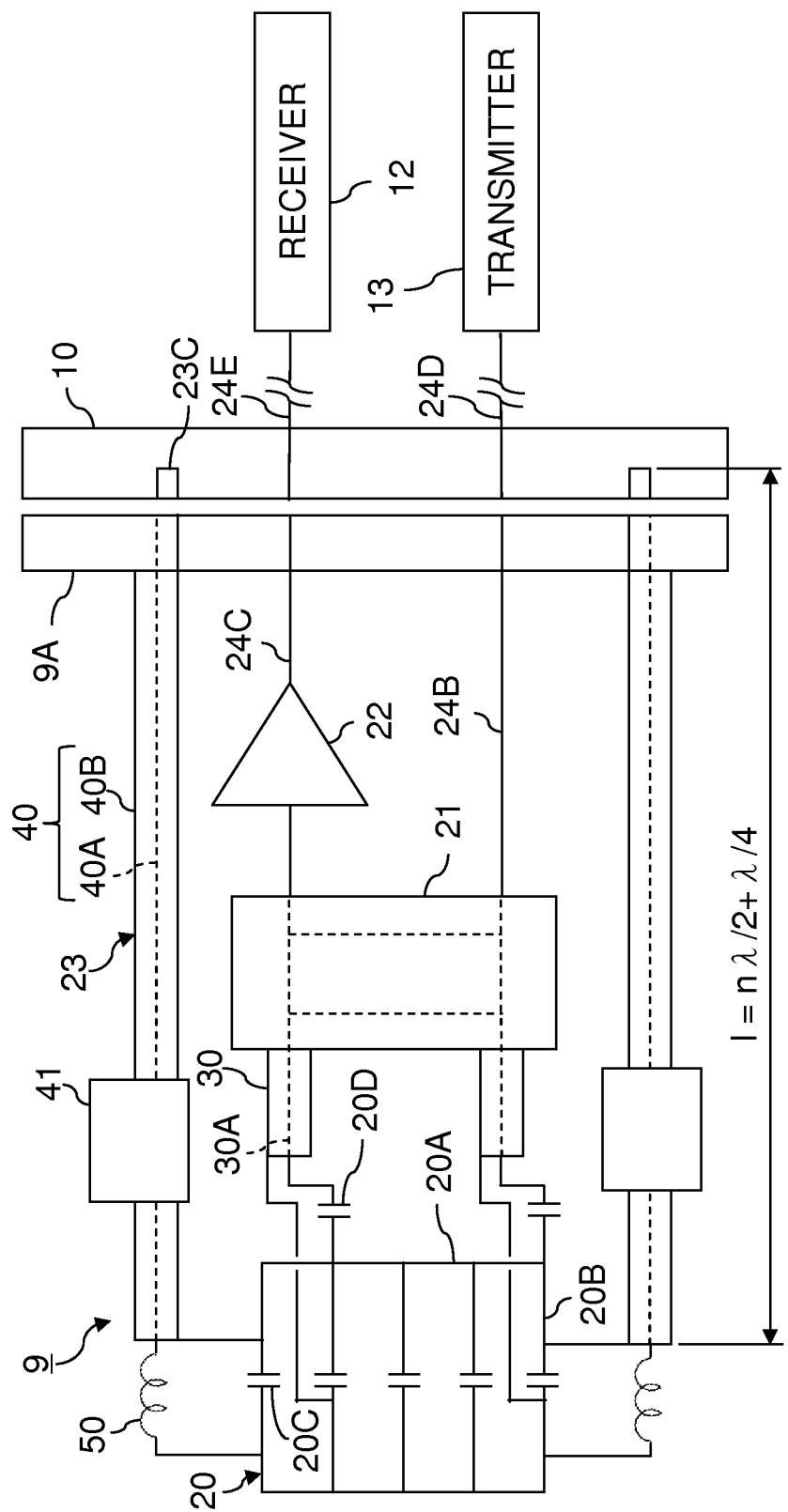
FIG. 11 is a view showing the ninth example of circuit configuration of the local RF coil shown in FIG. 1.

FIG. 11 is a view showing the ninth example of circuit configuration of the local RF coil 9 shown in FIG. 1.

The local RF coil 9 in the ninth example of circuit configuration shown in FIG. 11 has a circuit configuration similar to that of the local RF coil 9 in the fourth example of circuit configuration shown in FIG. 6. However, each breaker circuit 23 has an inductor 50. The inductors 50 are respectively connected between the condenser elements 20C to be broken targets and the central conductors 40A or the external conductors 40B in one ends of the coaxial cables 40. Furthermore, the inductances of the inductors 50 are determined according to the capacitances of the corresponding condenser elements 20C so that the inductors 50 resonate with the corresponding condenser elements 20C respectively. Then, the length 1 of each coaxial cable 40 is determined so as to satisfy the formula (2).

According to the local RF coil 9 which has the above-mentioned circuit configuration, when the coil connector 9A of the local RF coil 9 has not been connected to the system connector 10 in the control system 3 side, the resonance frequency of the local RF coil 9 can be detuned from the frequency of RF transmission pulses, similarly to the local RF coil 9 in the eighth example of circuit configuration shown in FIG. 10. That is, the respective condenser elements 20C can be broken from the local RF coil 9 by the parallel resonant circuits which consist of the condenser elements 20C and the inductors 50 respectively.

Note that, each of the examples shown in FIG. 2 to FIG. 11 and other examples of circuit configuration of the local RF coil 9 can be combined with each other. Namely, an appropriate number of the breaker circuits 23 can be connected with appropriate circuit elements respectively so that a desired portion or desired portions of the circuit which constitutes the local RF coil 9 do not contribute to the resonance frequency of the local RF coil 9 when the coil connector 9A of the local RF coil 9 has not been connected to the system connector 10 in the control system 3 side.

That is, the above-mentioned magnetic resonance imaging apparatus 1 is an apparatus of which the circuit of the local transmission RF coil 9 arranged and used in the WB coil 6 is configured to electrically break a part of the local RF coil 9 to change the transmission frequency of the local RF coil 9 when the coil connector 9A of the local RF coil 9 has not been connected to the system connector 10 in the MRI apparatus side.

Therefore, according to the magnetic resonance imaging apparatus 1, even in a case where the local RF coil 9 has been installed in the WB coil 6 without connecting the local RF coil 9 with the MRI apparatus side, generation of induced currents can be suppressed to avoid breakage of the local RF coil 9 due to a rise in temperature and secure the safety of a subject O.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, in the above-mentioned embodiments, a part of the circuit of the local RF coil 9 is configured to be broken mainly using the coaxial cable 40 having a predetermined length. However, an arbitrary circuit may be used as the breaker circuit 23 so long as the arbitrary circuit has a switching function which breaks a part of the circuit of the local RF coil 9 according to whether the coil connector 9A of the local RF coil 9 has been connected with the system connector 10 in the MRI apparatus side or not.

What is claimed is:

1. A magnetic resonance imaging apparatus comprising:
a data acquisition system configured to acquire magnetic resonance signals from a subject by applying a static magnetic field, a gradient magnetic field and a radio frequency magnetic field to an imaging area in which the subject is set; and
a control system configured to acquire the magnetic resonance signals by controlling said data acquisition system to generate image data based on the acquired magnetic resonance signals;
wherein said data acquisition system has:
a whole body coil configured to apply the radio frequency magnetic field to the imaging area;
a radio frequency coil configured to apply the radio frequency magnetic field to the imaging area when a radio frequency pulse has been applied from said control system through a connector, said radio frequency coil being set inside said whole body coil; and
a breaker circuit configured to electrically break a part of a circuit constituting said radio frequency coil when the connector of said radio frequency coil has been disconnected to said control system;
wherein said breaker circuit has:
a coaxial cable having a central conductor and an external conductor, said coaxial cable having one end connected with a part of said radio frequency coil while another end is connected to the connector of said radio frequency coil, the part being a broken circuit target; and
a short circuit configured to be connected with the other end of said coaxial cable through the connector to electrically connect the central conductor of said coaxial cable with its external conductor when the connector of said radio frequency coil has been connected to said control system.

2. A magnetic resonance imaging apparatus of claim 1, wherein said breaker circuit is configured to electrically break at least one of a condenser element and a conductor from said radio frequency coil.

3. A magnetic resonance imaging apparatus of claim 1, wherein said radio frequency coil has:
a coil element configured to transmit the radio frequency magnetic field when the radio frequency pulse has been applied from said control system through the connector, while to receive the magnetic resonance signals to output the magnetic resonance signals to said control system through the connector; and
a switching circuit configured to switch the radio frequency pulse and the magnetic resonance signals;
wherein said breaker circuit is configured to electrically break a circuit between said coil element and said switching circuit when the connector of said radio frequency coil has been disconnected from said control system.

4. A magnetic resonance imaging apparatus of claim 1, wherein said breaker circuit has:

coaxial cables having ends respectively connected with elements of the circuit constituting said radio frequency coil while each of other ends of the coaxial cables are connected with the connector of said radio frequency coil, the elements corresponding broken circuit targets; and a short circuit configured to be connected between central conductors and external conductors of the coaxial cables at each of the other ends of said coaxial cables through the connector when the connector of said radio frequency coil has been connected to said control system.

5. A magnetic resonance imaging apparatus of claim 1, wherein said breaker circuit has an inductor connected between the central conductor or the external conductor in the one end of said coaxial cable and a condenser element as the broken circuit target, the inductor resonating with the condenser element.

* * * * *